United States Patent [19]

Derrieu et al.

[11] Patent Number: 5,683,722
[45] Date of Patent: Nov. 4, 1997

[54] ORALLY-ADMINISTERED DOSAGE FORM FOR ANIMALS, PREPARATION METHOD THEREFOR AND USES THEREOF

[75] Inventors: Guy Derrieu, Cagnes Sur-Mer; André Aubert, Opio; Bernard Raynier, Nice; Carolin L. Schumacher, Vence, all of France

[73] Assignee: Virbac S.A., Carros, France

[21] Appl. No.: 637,642

[22] PCT Filed: Oct. 27, 1994

[86] PCT No.: PCT/FR94/01251

§ 371 Date: Aug. 1, 1996

§ 102(e) Date: Aug. 1, 1996

[87] PCT Pub. No.: WO95/11665

PCT Pub. Date: May 4, 1995

[30] Foreign Application Priority Data

Oct. 29, 1993 [FR] France .................. 93 12954

[51] Int. Cl.$^6$ .................................................. A61K 9/14
[52] U.S. Cl. .................. 424/493; 424/494; 424/495; 424/497; 424/498
[58] Field of Search .................... 424/489, 438, 424/464, 493, 494, 495, 497, 498

[56] References Cited

FOREIGN PATENT DOCUMENTS

| | | |
|---|---|---|
| 0475536A1 | 1/1988 | European Pat. Off. . |
| 0458751A1 | 5/1990 | European Pat. Off. . |
| 0 458 751 | 11/1991 | European Pat. Off. . |
| 0 475 536 | 3/1992 | European Pat. Off. . |

*Primary Examiner*—Thurman K. Page
*Assistant Examiner*—William E. Benston, Jr.
*Attorney, Agent, or Firm*—Lowe, Price, LeBlanc & Becker

[57] ABSTRACT

A dosage form for orally administering chemical or medicinal substances such as vitamins, trace elements, amino acids, nutritive substances, vaccines, etc., to domestic or wild animals, and a method for preparing same, are disclosed. Said dosage form includes: a porous water-soluble central core containing binders selected from polypeptides, polysaccharides, polymers and colloids, and/or diluents selected from polyols, metal oxides, carbonates, phosphates and microcrystalline cellulose, and an effective amount of at least one bioactive substance; and a palatable hydrophobic outer layer containing at least one lipid substance selected from fatty alcohols, fatty acids, glycerol esters, hydrogenated oils, waxes, paraffin, lanolin, coconut oil and fatty acid salts; a polymeric agent for modulating the disintegration and adhesion of said outer layer, and natural or synthetic palatable substances.

13 Claims, No Drawings

ORALLY-ADMINISTERED DOSAGE FORM FOR ANIMALS, PREPARATION METHOD THEREFOR AND USES THEREOF

The present invention relates to a dosage form designed to allow the oral administration of chemical or medicinal substances, such as vitamins, trace elements, amino acids, nutritive substances, vaccines, and the like, to domestic or wild animals.

The present invention also relates to the method for producing the said dosage forms.

Systems which allow the oral administration of medicaments to domestic animals or to animals reared intensively, or to wild animals, which are difficult or dangerous to restrain, are already known.

Such systems are the subject of patent applications or patents (Patent EP 0 240 826, Patent EP 0 208 528 and Patent Application EP 0 421 863).

The bait described in Patent EP 0 240 826 is obtained by a first casting, at the bottom of the mould, of a support, comprising a lipid compound (having a melting point of between 20° and 60° C.), a compound designed to stabilize the shape of the bait and an attractive and palatable compound for the animals, introducing the active substance on the solidified support layer, and then a second casting of the said support, so as to cover completely the said active substance.

The system has the disadvantage of exhibiting low mechanical strength and brittleness in the vicinity of the junction of the two castings and makes it unsuitable for large-scale distribution methods (aerial release, for example, for treating large numbers of wild animals, over large areas).

Patent EP 208 528 describes a bait for fish and crustacea consisting essentially of a water-insoluble polymer having a melting point of less than 110° C. (polyamides or ethylene copolymers, EVA, in particular), of an attractive substance and of edible oil or of molasses (0 to 20%).

The bait according to this Patent EP 208 528 are obtained by extrusion at 90°–110° C. of a dry mixture of the polymer, the attractive substance and optionally the edible oil.

International Application WO 89/12393 describes pesticidal compositions comprising EVA, a bioactive agent, a source of proteins/sugars/lipids and optionally 0 to 20% edible oil, an attractive substance, a colorant, a preservative, a repelling agent and a biomarker.

The compositions according to this International Application PCT WO 89/12393 may be in the form of blocks or of tablets and are also prepared by extrusion of the above-mentioned composition, either by melting the polymer (capable of melting at a temperature<110° C.) followed by the mixing of the latter with the other ingredients, or by heating, up to the melting point of the polymer, a mixture of all the ingredients in a dry form.

Patent Application EP 421 863 describes systems comprising two parts: an envelope in tubular form, obtained by extrusion and comprising at least one attractive substance, at least one agglomerating substance (polysaccharides, starches or polymers such as EVA) and optionally a hydrophobic substance (oil) and inside the cavity of the envelope, a binding substance (mixture of fatty substances having a melting point which is not too high) containing an active ingredient, the binding substance taking the internal shape of the envelope. Such an envelope has a high mechanical and thermal strength which allows, in particular, distribution by aerial release.

The compositions or systems of the prior art are generally designed such that they have a good resistance to handling and to shocks and/or good attractiveness for animals, facilitating the effective consumption of the active ingredient(s) included in these systems.

However, in general, the compositions described in these documents do not allow the active ingredients a residence time in the buccal cavity sufficient to ensure the efficacy of some drugs or when it is essential to obtain a certain contact time, especially for certain treatments. Furthermore, they do not ensure for the active ingredients sufficient stability, in particular those of biological origin.

Application EP 458 751 describes a system comprising a central core comprising cyclic amino acids, a first coating composed of a polymer capable of forming a film (5%–100% of the core by weight) and a hydrophobic second coating consisting of lipids (20%–400% by weight of the core+first coating combination) allowing the production of granules, essentially intended to be subjected to further processing; in addition, such systems induce a controlled release of the active ingredient and do not make it possible to process and stabilize products of biological origin in aqueous solution or suspension.

The aim of the present invention is, consequently, to provide a new dosage form which is better suited to the requirements encountered in the treatment of certain conditions, in the administering of certain treatments, in the execution of certain medical acts on animals, such as for example oral vaccination or treatments of the buccal cavity, than the compositions and systems of the prior art.

The subject of the present invention is a dosage form for orally administering chemical or medicinal substances, of the type comprising a solid central core containing one or more bioactive substances and an outer layer or coating, characterized in that:

the porous water-soluble central core comprises:
at least one substance chosen from the group which comprises the binders selected from polypeptides, high molecular weight polysaccharides, polymers capable of giving colloidal solutions and colloids, and diluents selected from polyols, metal oxides, carbonates, phosphates or microcrystalline cellulose, the overall quantity of binder and diluent being between 50 and 98% by weight relative to the said central core, and
an effective quantity of at least one bioactive substance, and the palatable hydrophobic outer layer comprises:
at least one lipid substance chosen from fatty alcohols (cetyl alcohol, stearyl alcohol), fatty acids (stearic acid, palmitic acid), glycerol esters such as glycerol palmitostearate, glycerol stearate (marketed under the trade mark PRECIROL), glycerol behenate (marketed under the trade mark COMPRITOL), hydrogenated oils such as hydrogenated castor oil (marketed under the trade mark CUTINA HR), waxes or fatty substances such as carnauba wax, beeswax, paraffin, lanolin, coconut oil and fatty acid salts such as calcium or magnesium stearate:
an agent for modulating the disintegration of the said outer layer and the adhesion of the microparticulate fragments derived from the disintegration of the central core, soluble or dispersible in the lipid mass, chosen from polymers selected from the group which comprises acrylic resins (marketed under the trade mark EUDRAGIT), polyvinyl acetates (marketed under the trade mark RHODOPAS), polyalkylene resins, ethylene/vinyl acetate (EVA) copolymers, crosslinked polymers of starch, dextran, insulin or vinylpyrrolidone and cellulose derivatives selected from hydroxypropyl cellulose, hydroxypropyl methylcellulose, ethyl cellulose, carboxymethylcellulose; and natural or synthetic palatable substances of purely plant origin or containing products of animal origin, chosen from meat or fish meals, flavours such as boiled beef flavour, roast pork flavour, white fish flavour, groundnut flavour, bacon flavour, liver flavour.

This dosage form is therefore composed of a double compartment. The first compartment, in the middle, is a porous solid central core having the characteristic of dissolving or of disintegrating rapidly in an aqueous medium or in saliva. The micro-particulate fragments or aggregates generated by this disintegration are likely to adhere to the tissues of the buccal cavity because of the specific composition of the form according to the invention.

The second compartment is in fact a film or envelope both of a lipid and polymeric nature, hydrophobic, palatable and of controlled thickness which ensures:

easy handling of the dosage form according to the invention, without modifying the integrity of the water-soluble central compartment of porous structure, protection of the central core against moisture, protection against contamination of the person responsible for administering the product, in particular for oral vaccination, attractiveness for the target animal, good thermal resistance to temperatures of between −30° C. and +45° C., without modification of the texture or lipid exudation, optimum stability of the solid and dry central core, and therefore of the sensitive bioactive molecules, stability over time, the physical characteristics being unalterable, during the stay in the distribution medium, more particularly for animals reared intensively, and bioadhesion to the mucous membranes of the buccal cavity and immediate availability of the active ingredients across them, which leads to optimum bioavailability, whereas tablets or other bait according to the prior art have a content which is too compact or too fluid to allow persistence in the buccal cavity.

Active ingredient is understood to mean any biologically active material and more especially any molecule which may exhibit difficulties of formulation linked to problems of taste, low solubility or insolubility, instability, or to a low bioavailability.

The dosage form according to the invention may be used for the administration of all sorts of substances, commonly used in veterinary medicine and more particularly oral vaccines, nutritional agents, agents for regulating metabolisms, contraceptives, plant extracts, food adjuvants, hygiene and dietetic agents, and cosmetic agents. This new form allows, in addition, a solid presentation of liquid active ingredients.

By way of example, among the active substances administrable in this form, there may be mentioned:

antibiotics such as betalactamines (amoxicillin, ampicillin, cefalexin), chloroamphenicol, macrolides (josamycin, erythromycin, spiramycin, tylosin), tetracyclines, anti-infectious agents other than antibiotics such as furans, quinolones, sulphamides, sulphones, trimethoprim, anti-inflammatory agents such as corticoids, pyrazoles, salicylates, non-steroids, antimycotics such as griseofulvin, ketonazole, anthelminthics such as oxybendazole, pyrantel, mebendazole, oxfendazole, fenbendazole, netobimin, nutritional agents such as oral rehydrating agents, amino acids (methionine, lysine), products which supply energy, minerals or vitamins, local gingivodental products, antiseptics, antibacterials, such as hexamidine, chlorohexidine, hexitidine, and breath modifiers, antiviral, antibacterial, antiparasitic vaccines, in the following forms:
inactivated: complete antigen
live attenuated
live mutated avirulent
live derived from genetic recombination (viral, bacterial, plasmid vectors)
subunits: (glycoprotein; nucleoprotein)
purified recombinants: pure antigenic molecules
peptides
nucleic acid compounds
compounds of biological molecules associated with various cytokines: IL2, IL6, IL12, interferon; TNF . . .

antisense nucleosides
monoclonal antibodies, anti-idiotypic or otherwise specific cellular receptors
cytokines,
anti-cancer agents,
growth factors,
contraceptive vaccines, hormonal or otherwise,
biological insecticides,
adjuvants
non specific for immunity
specific for TH1 (cellular immunity)
specific for TH2 (humoral immunity),
transgenics-supporting factors,
local attachment or anti-attachment factors (mucous membranes, intestinal villosities . . . ).

Binder is understood to mean a thickening and structuring substance serving as support, soluble or disperible in water, which makes it possible to ensure the cohesion of the mass, inert in relation to the active ingredient(s) and capable of enhancing the adhesion of microparticulate fragments of the central core to the mucous membranes of the buccal cavity, after the effective consumption of the said dosage form by the animal.

These binders are especially chosen from polypeptides such as gelatin or partially hydrolyzed gelatin, polysaccharides of high molecular weight, polymers capable of giving colloidal solutions and colloids, such as natural or synthetic gums (gum arabic, karaya gum, xanthan gum, guar gum, carob gum), alginates, cellulose derivatives such as sodium carboxymethylcellulose, hydroxypropyl methylcellulose, pectinates, carageenans, dextrans, homo- or copolymers of acrylic acid, water-dispersible derivatives of starch, colloidal silicas, polyvinyl alcohol, polyvinylpyrrolidone, polyethylene glycols (particularly PEG 6000 and 8000), or alternatively mixtures of the said binders.

Advantageously, these binders are more particularly chosen from gum arabic, xanthan gum, pectin, natural biopolymers commonly used in the preparation of tablets or chewing gums to enhance bioadhesion to the mucous membranes of the buccal cavity.

Diluent denotes pharmaceutically acceptable substances, preferably water-soluble, which enhance the physical properties of the central core. These substances may be chosen especially from mannitol, xylitol, lactose, glycine, sorbitol, glucose, maltodextrins, cyclodextrins or alternatively from oxides (magnesium oxide), carbonates (calcium carbonate), phosphates (tricalcium phosphate), microcrystalline cellulose.

According to an advantageous embodiment of the said dosage form, the central core comprises, in addition, one or more additives chosen from taste modifying or masking substances such as saccharine, saccharinates, cyclamates, aspartame, disintegration-modulating agents like silica, absorption promoters such as cyclodextrins or glycyrrhetinic acid salts, surface-active agents chosen from nonionic or cationic surfactants, such as sorbitan esters, propylene and ethylene oxide copolymers, fatty alcohol and polyoxyethylene ethers, colorants and preservatives.

The central core therefore contains at least one substance chosen from the binders and diluents listed above, but it may contain one or more binders and/or one or more diluents.

According to another advantageous embodiment of the said dosage form, the lipid substance of the said outer layer is chosen from paraffin, coconut oil, palmitic acid and glycerol esters and the agent for modulating the disintegration of the said outer layer is chosen from ethylene/vinyl acetate copolymers and cross-linked polysaccharides.

In accordance with the invention, the outer layer or hydrophobic barrier of the dosage form according to the invention may also contain:

inorganic substances chosen from the group which comprises inorganic oxides selected from the oxide of titanium and iron, phosphates, carbonates, clays and talc, which substances also act on the rate of disintegration of the said outer layer and/or a surfactant chosen for example from sorbitol esters, polyoxyethylene polysorbates (marketed under the trade mark TWEEN), lecithins, sorbitan esters, in order to ensure the homogeneity and the processing of the mixture constituting it when the latter is present in the form of a suspension during the operation of film-coating (coating) of the central core. This hydrophobic material may advantageously contain fatty acid and glycerol esters, such as mono- and (or) diglycerides, whose major influence will be to increase the affinity between the lipid layer and the central core, thus enhancing the adhesion between the two compartments of the dosage form according to the invention. The flexibility and the relative elasticity of the film-forming material is thereby enhanced.

In accordance with the invention, the said dosage form advantageously comprises:

| central core: | |
| --- | --- |
| diluents and/or binders | 50 to 98% |
| bioactive substances | 0.25 to 50% |
| other additives | 0 to 1.75% |
| outer layer: | |
| lipid substances | 40 to 93% |
| polymers | 4 to 30% |
| palatable substances and other additives | 3 to 30% |

The subject of the present invention is also a method for the preparation of the dosage form in accordance with the invention, characterized in that the following operations are carried out:

a) preparation of a paste containing the various constituents of the central core, namely bioactive substances, diluents, binders and optionally one or more additives and a quantity of water suitable to adjust the homogeneity and the viscosity of the suspension obtained, b) solidification of the product obtained in a), c) coating of the products obtained in b), with a mixture in solution or in suspension, comprising at least one lipid substance, one agent for modulating the disintegration of the outer layer and one palatable substance.

More precisely, the preparation of the central core is carried out according to the following operations:

a) preparation of a paste containing the various constituents listed further above, as well as a suitable quantity of water to give the suspension obtained rheological characteristics allowing optimum processing;

b) solidification of the product obtained in a), especially by freezing and sublimation (freeze-drying) in particular when the active ingredient is a vaccine, or an equivalent operation.

According to an advantageous embodiment of the said process, the said solidification is carried out by a physical operation such as evaporation, drying or freeze-drying.

When the solidification is carried out by evaporation, the latter is carried out under reduced pressure and preferably combined with exposure to ultrahigh frequencies. This processing, performed for example in a VRIECO-NAUTA or VACTRON mixer-dryer (MACHINES COLETTE), will be preferred when it is desired to obtain a unit which has a spherical shape or an overall spherical shape, the conditions of use making it possible to control the mean size of the central core according to the invention.

When the solidification is carried out by freeze-drying, the paste obtained in a) is preferably divided into unit quantities having a shape and volume which are determined before freezing and sublimation.

It is understood that the division of the product can also be carried out mechanically after freeze-drying, but it is advantageous to distribute the paste into cells having a shape and size determined prior to the freeze-drying operation.

In accordance with the invention, the active ingredient(s) will be soluble or will be in suspension in the paste to be distributed, in free form or in the form of microparticles or nanoparticles. The latter form, more particularly adapted to solidification by freeze-drying, can avoid the complete and immediate release of the active ingredient when brought into contact with aqueous media and the flow of saliva. Bioresorbable polymers or macromolecular substances enter into the constitution of micro- or nanoparticles.

The coating of the central core previously described is carried out according to the customary techniques commonly used in the pharmaceutical and food industries. Depending on the shape and the size of the central core, there will be more particularly used coating by evaporation of the solvent, coating by coacervation, turbine film-coating, fluidized bed coating or coating by dipping which is widely used in the food industry, more specifically the confectionery industry.

The dosage form in accordance with the invention is most particularly indicated:

for oral pharmaceutical formulations for which it is advisable to mask the taste of the bioactive substances, for buccal bioadhesion formulations, such as for example breath freshening systems, for formulations including active ingredients sensitive to the mechanisms of digestion and whose passage through the mucous membranes of the buccal cavity will be stimulated.

In addition to the preceding features, the invention further comprises other features which will emerge from the following description, which refers to examples of carrying out the methods which is the subject of the present invention.

It should be clearly understood, however, that these examples are given purely by way of illustration of the subject of the invention and do not constitute in any manner a limitation thereto.

EXAMPLE I

Unit form for dental hygiene.

A premix containing the active ingredients and excipients and having the following composition:
Chlorhexidine diacetate . . . 0.25%
Methionine . . . 3%
Lactose . . . 80%
β-cyclodextrin . . . 13%
Dextran 70 . . . 2%
Pulverized silica . . . 0.25%
Aspartame . . . 0.8%
Sorbitan monopalmitate . . . 0.7%
is prepared in an OLSA-type planetary mixer.

The pulverulent mass is dry mixed for 30 minutes and then supplemented with water in an amount of 38 g per 100 g of dry mass, and blended for 1 hour at room temperature. The homogeneous suspension thus obtained is distributed into 1.5 cm$^3$ polyvinyl chloride cells. The cellular sheet containing the suspension is introduced into a freeze-dryer immediately after division, to be frozen at a temperature of −45° C. under atmospheric pressure, for about 3 hours. After drying for 12 hours under reduced pressure at a negative temperature, the temperature is increased to 30° C. in steps of 5° C. The freeze-dried unit, extracted from the cell, is treated in a fluidized bed (GLATT GPC-15) with injection of air (100 liters/min, at 30°–5° C.), with a solution of hydrogenated castor oil (1 part), ethyl cellulose (2.5 parts), beeswax (3 parts), cetyl alcohol (1 part), groundnut flavour (0.15 part) in methylene chloride (80 parts), maintained at 25°–30° C.

EXAMPLE II

Unit form for oral vaccination against rabies in dogs.

Carrying out the procedure as described above for Example I, a dry mixture is used which has the following composition:
Lactose . . . 28%
Mannitol . . . 70%
Gum arabic . . . 2%

A vaccinal suspension of SAG-2 strain of sufficient titre to ensure immunity of the vaccinated animal is added at the rate of 40 g per 100 g of dry mass and the procedure is carried out as described above. The freeze-dried unit, extracted from the cell, is coated by dipping in a homogeneous mixture maintained at 56°–60° C., of the following composition: paraffin 50°–2° C. (52%), ethylenevinyl acetate copolymer at 28% vinyl acetate (6%), meat meal (23%), beef fat (17%), ROBERTET bacon flavour (2%). A dosage form according to the invention suitable for oral vaccination is thus obtained.

EXAMPLE III:

A mixture having the following composition:
Lactose . . . 20%
Mannitol . . . 45%
Polyvinylpyrrolidone K 30 . . . 6%
Dicalcium phosphate . . . 5%
Sulphamethoxypyridazine . . . 20%
Trimethoprim . . . 4%
Water . . . 45% per 100 g of dry matter
is prepared in a planetary mixer-dryer capable of withstanding reduced pressure and equipped with a generator of ultrahigh frequencies.

The mixture is mixed for 1 hour and then the water is removed under vacuum with the aid of microwaves (discontinuous excitation with generators of power varying between 1 and 4 KW), not exceeding 40° C. The granules obtained are coated in a fluidized bed by spraying of a solution containing 5% Eudragit$^R$ L 100, containing a small quantity of fatty acid monoglyceride and anhydrous silicic anhydride, in a 1/1 mixture of methylene chloride and isopropanol, at the rate of 30 ml/min.

EXAMPLE IV

Tests in vitro and in vivo of the dosage forms in accordance with the invention obtained according to Examples I and II.

a) Temperature behaviour

The tests showed that at temperatures of between −30° C. and +45° C., there was no modification of the appearance or of the structure. The dosage form, placed on an absorbent paper stored at 45° C., softens very slightly, without showing any exudation, or spot of fat on the paper; in addition, the physical characteristics of the freeze-dried central core are not modified.

b) Attractiveness, palatability and bioadhesion

The tests of attractiveness were performed on two groups of nine dogs (three small, three medium, three large), by presenting respectively the dosage form according to Example I (group A), the central core according to Example I (group B), having taken care to introduce Rhodamine B used as marker in an amount of 0.2% (w/w). The results are very favourable, with an immediate consumption of 100% and 80% respectively for groups A and B. It should be noted that, for group B, the consumption is effective for the remaining 20% within 10 minutes following the presentation. The tests of palatability and bioadhesion are performed on groups A and B and a comparable group C, to which a conventional tablet of similar composition to the dosage form according to Example I is presented. The results are very favourable for the dosage form according to the invention, with a mean intensity of the colour of the buccopharyngeal cavity (increasing scale of 0 to 4) of 4, 4 and 2 respectively for groups A, B and C.

c) Stability

The tests carried out in b) were repeated with forms which are identical but stored for 6 months at 4° C. The results are quite comparable. A study of the stability of the dosage form according to Example II was conducted by monitoring the titre of the vaccinal suspension, as a function of time and of storage temperature. This study was carried out in parallel in comparison with a control batch of vaccinal suspension, stored in liquid form and packaged in blisters. The controls are carried out within 7, 14 and 28 days, 3 and 6 months following the preparation of the suspension and of the corresponding dosage form. The weekly fall in the cytopathogenic infectious dose destroying 50% of the cells (CPID50) is expressed in relation to the two preparations. The results are assembled in Table I and show the specific benefit of the dosage form compared with a conventional preparation.

TABLE I

| composition | Storage temperature | | | | |
|---|---|---|---|---|---|
| | −80° C. | −20° C. | +4° C. | +25° C. | +35° C. |
| Liquid SAG-2 in blisters | 0 | −0.025* | −0.19 | −0.76 | −1.82 |
| Dosage form according to Example II | 0 | 0 | −0.05 | −0.1 | −0.3 |

*: fall in the CPID 50 expressed in log/week d) Efficacy

A study was carried out with the dosage form according to Example II in comparison with conventional dog bait having the vaccinal amount in liquid form in blisters. The 14 dogs selected are divided into 4 groups A, B, C and D. Group A (4 dogs). receives the dosage form according to the invention, group B (4 dogs) receives the freeze-dried central core (without the protective compartment), group C (4 dogs) receives a conventional bait, and group D (2 dogs) is not treated. The dogs are monitored for 30 days, controlling the variation in the level of anti-rabies antibodies. At 30 days, the seroconversion levels are greater than 0.5 IU for 4, 3 and 3 dogs, respectively in groups A, B and C. These results show the stability and the efficacy of the dosage form according to the invention.

As evident from the above, the invention is not in the least limited to its implementations, embodiments and applications which have just been described more explicitly; on the contrary, it embraces all the variants thereof which may occur to a specialist in this field without departing from the framework or the scope of the present invention.

We claim:

1. Dosage form for orally administering chemical or medicinal substances, comprising a solid central core containing one or more bioactive substances and an outer layer or coating, wherein:

said central core being porous and water-soluble and comprising:

at least one substance selected from the group consisting of binders selected from the group consisting of polypeptides, high molecular weight polysaccharides, polymers capable of giving colloidal solutions and colloids, and diluents selected from the group consisting of polyols, metal oxides, carbonates, phosphates or micro-crystalline cellulose, the overall quantity of binder and diluent being between 50 and 98% by weight relative to the said central core, and an effective quantity of at least one bioactive substance, and said outer layer comprising:

at least one lipid substance selected from the group consisting of fatty alcohols, fatty acids, glycerol esters, hydrogenated oils, waxes, paraffin, lanolin, coconut oil and fatty acid salts;

an agent for modulating the disintegration and the adhesion of the said outer layer, soluble or dispersible in the lipid mass, selected from the group consisting of polymers selected from the group consisting of acrylic resins, polyvinyl acetates, polyalkylene resins, ethylene/vinyl acetate (EVA) copolymers, cross-linked polymers of starch, dextran, insulin or vinylpyrrolidone and cellulose derivatives selected from the group consisting of hydroxypropyl cellulose, hydroxypropyl methylcellulose, ethyl cellulose, carboxymethylcellulose; and natural or synthetic palatable substances selected from the group consisting of products of purely plant origin, products of animal origin selected from the group consisting of meats or fish meals, and flavours.

2. Dosage form according to claim 1, wherein the central core further comprises one or more additives selected from the group consisting of taste modifying or masking substances, disintegration-modulating agents, absorption promoters, surface-active agents chosen from nonionic or cationic surfactants, colorants and preservatives.

3. Dosage form according to claim 1, wherein the outer layer further comprises inorganic substances selected from the group consisting of inorganic oxides, phosphates, carbonates, clays and talc and/or a surfactant selected from the group consisting of sorbitol esters, polyoxyethylene polysorbates, lecithins and sorbitan esters.

4. Dosage form according to claim 1, wherein the diluents and binders of the inner core are selected from the group consisting of gum arabic, xanthan gum, pectin, sorbitol, xylitol and mannitol type polyols and mixtures thereof.

5. Dosage form according to claim 1, wherein the lipid substance of said outer layer is selected from the group consisting of paraffin, coconut oil, palmitic acid and glycerol esters, and wherein the agent for modulating the disintegration of said outer layer is selected from the group consisting of ethylene/vinyl acetate copolymers and cross-linked polysaccharides.

6. Dosage form according to claim 1, wherein the bioactive substances of the inner core are selected from the group consisting of vaccines, cytokines, anti-cancer agents, growth factors, immunity adjuvants, transgenics-supporting factors, local attachment or anti-attachment factors.

7. Dosage form according to claim 6, wherein the inner core comprises, as bioactive substance, a vaccine selected from the group consisting of antiviral vaccines, antiparasitic vaccines, antibacterial vaccines and contraceptive vaccines.

8. Dosage form according to claim 6, wherein the inner core comprises, as bioactive substance, an anti-rabies vaccinal suspension of strain SAG-2.

9. Dosage form according to claim 1, characterized in that it has the following formula:

| central core: | |
|---|---|
| diluents and/or binders | 50 to 98% |
| bioactive substances | 0.25 to 50% |
| other additives | 0 to 1.75% |
| outer layer: | |
| lipid substances | 40 to 93% |
| polymers | 4 to 30% |
| palatable substances and other additives. | 3 to 30% |

10. Medicinal product comprising a dosage form according to any one of claims 1 to 9.

11. Immunological vector comprising a dosage form according to claim 1.

12. Dietetic product comprising a dosage form according to claim 1.

13. Food product comprising a dosage form according to claim 1.

* * * * *